(12) United States Patent
Calderoni et al.

(10) Patent No.: US 8,430,175 B2
(45) Date of Patent: Apr. 30, 2013

(54) EQUIPMENT FOR INTERCEPTING AND DIVERTING A LIQUID CIRCULATION FLOW

(75) Inventors: Angelo Calderoni, San Donato Milanese (IT); Giorgio Girola, Cislago (IT)

(73) Assignee: ENI S.p.A., Rome (IT)

( * ) Notice: Subject to any disclaimer, the term of this patent is extended or adjusted under 35 U.S.C. 154(b) by 612 days.

(21) Appl. No.: 12/526,181

(22) PCT Filed: Jan. 30, 2008

(86) PCT No.: PCT/EP2008/000817
§ 371 (c)(1),
(2), (4) Date: Oct. 23, 2009

(87) PCT Pub. No.: WO2008/095650
PCT Pub. Date: Aug. 14, 2008

(65) Prior Publication Data
US 2010/0084142 A1 Apr. 8, 2010

(30) Foreign Application Priority Data
Feb. 8, 2007 (IT) .............................. MI2007A0228

(51) Int. Cl.
*E21B 19/08* (2006.01)
(52) U.S. Cl.
USPC ........ 166/380; 166/77.1; 166/80.1; 166/90.1; 175/162
(58) Field of Classification Search .................. 166/380, 166/386, 81.1, 80.1, 90.1, 77.1, 77.51; 175/57, 175/162
See application file for complete search history.

(56) References Cited

U.S. PATENT DOCUMENTS

| | | | | |
|---|---|---|---|---|
| 3,215,203 A | * | 11/1965 | Sizer | 166/77.4 |
| 3,559,739 A | * | 2/1971 | Hutchison | 166/311 |
| 3,889,959 A | * | 6/1975 | Persson | 277/324 |
| 3,999,610 A | * | 12/1976 | Sage et al. | 166/383 |
| 4,315,553 A | * | 2/1982 | Stallings | 175/207 |
| 4,643,259 A | * | 2/1987 | Zeringue, Jr. | 166/77.51 |
| 5,568,837 A | * | 10/1996 | Funk | 166/383 |
| 5,832,956 A | | 11/1998 | Nimberger | |
| 6,315,051 B1 | * | 11/2001 | Ayling | 166/380 |
| 6,374,925 B1 | * | 4/2002 | Elkins et al. | 175/25 |

(Continued)

FOREIGN PATENT DOCUMENTS

| | | |
|---|---|---|
| WO | 01 69034 | 9/2001 |
| WO | 2005 108831 | 11/2005 |
| WO | 2006 133826 | 12/2006 |

*Primary Examiner* — Jennifer H Gay
(74) *Attorney, Agent, or Firm* — Oblon, Spivak, McClelland, Maier & Neustadt, L.L.P.

(57) ABSTRACT

Equipment for intercepting and diverting liquid circulation flow includes three chambers and a series of valves. The chambers are equipped with a connection device with arrival or supply lines, communicating with each other, of which only a first chamber communicates with second and third chambers. Communication between the first and second chambers and between the first and third chambers each is obtained by at least two valves, one is a flow-rate valve and at least one is an equalizer valve. An upstream or downstream of each equalizer valve is coupled with a fixed or adjustable flow-blocking device. The second and third chambers do not communicate and include a three-way valve in common with each other, or include two one-way valves in counterposition. One one-way valve is open when the other is closed and vice versa, and the three-way valve or the two one-way valves are coupled with a discharge valve.

7 Claims, 8 Drawing Sheets

Use of E-CD valve with the help of the E-CD Manifold

U.S. PATENT DOCUMENTS

| | | | |
|---|---|---|---|
| 6,412,554 B1 | 7/2002 | Allen et al. | |
| 6,527,062 B2 * | 3/2003 | Elkins et al. | 175/25 |
| 6,581,692 B1 * | 6/2003 | Koch et al. | 166/380 |
| 6,591,916 B1 * | 7/2003 | Ayling | 166/380 |
| 6,688,394 B1 * | 2/2004 | Ayling | 166/380 |
| 6,739,397 B2 * | 5/2004 | Ayling | 166/380 |
| 7,107,875 B2 * | 9/2006 | Haugen et al. | 81/57.15 |
| 7,252,151 B2 * | 8/2007 | Ayling | 166/380 |
| 7,322,418 B2 * | 1/2008 | Ayling | 166/380 |
| 7,487,839 B2 * | 2/2009 | Boscher et al. | 166/379 |
| 7,823,634 B2 * | 11/2010 | Chan et al. | 166/86.3 |
| 7,845,433 B2 * | 12/2010 | Calderoni et al. | 175/317 |
| 8,016,033 B2 * | 9/2011 | Iblings et al. | 166/244.1 |
| 8,100,199 B2 * | 1/2012 | Braddick | 175/218 |
| 2002/0134555 A1 * | 9/2002 | Allen et al. | 166/377 |
| 2004/0154835 A1 * | 8/2004 | Allen et al. | 175/170 |
| 2005/0236051 A1 | 10/2005 | McBeth et al. | |
| 2006/0278434 A1 | 12/2006 | Calderoni et al. | |
| 2010/0084142 A1 * | 4/2010 | Calderoni et al. | 166/380 |
| 2010/0236791 A1 * | 9/2010 | Askeland et al. | 166/380 |
| 2010/0252272 A1 * | 10/2010 | Haughom | 166/373 |

* cited by examiner (Background Art)
Fig. 1

Primary flow "F"

Axial valve "B"

Radial valve "A" with safety top

Pipe-shaped short body "C"

Drill pipe "P" (drill rod)

(Background Art)
Fig. 2

Axial valve "B" CLOSED

Radial valve "A" OPEN

Fast connector

Flexible pipe "F" (high pressure)

Probe plane

Rig pump Manifold - valve system existing on the drill plant

EQUIPMENT FOR INTERCEPTING AND DIVERTING A LIQUID CIRCULATION FLOW

BACKGROUND OF THE INVENTION

I. Field of the Invention

The present invention relates to equipment for intercepting and diverting a liquid circulation flow and the relative interception and diversion process.

II. Description of Related Art

This equipment can be used for exerting the function of diverting for safety purposes, during the insertion of a new drill string, the mud flow towards the device, called E-CD, described in patent application IT-MI2005A001108 of the same applicant, without influencing the Rig Pump Manifold of the Rig Contractor which therefore maintains its functional characteristics intact (it does not wear and is not modified).

Ever since the beginning of drilling called "rotary drilling" which dates back to over a century ago, which had replaced the advance technique called "percussion" in use at that time, introducing the novelty principle of the use of drill rods for transmitting the rotary movement to the bit (associated with the pumping of a fluid into the well through the same "battery" of rods), there has been the problem of interrupting the pumping process every time it was necessary to add a new rod to the battery, for drilling.

This time transitory, identified from the moment in which the pumping of fluid into the well is interrupted to the moment in which the pumping action into the well is re-started, after adding a new single element to the battery of rods, has always been considered a critical period. This critical period remains until the condition existing at the moment prior to the interruption of the pumping of fluid into the well has been re-established.

Some of the undesired effects caused by the conventional interruption of the fluid circulation in wells, during the insertion and connection, or disconnection, process of an element in a drill battery, are listed hereunder:

- there is a lack of dynamic pressure induced in the well by the circulation and its effect conventionally defined ECD (Equivalent Circulating Density) diminishes;
- the dynamic pressure induced at the well bottom is annulled, favouring the potential entry of layer fluids in the well (kick);
- when the circulation is restarted, after the rod has been added using a conventional method, troublesome overloads can be created of the more receptive formations, or potential circulation losses in the weaker formations;
- in high verticality wells the unobstructed and rapid falling of drill cuttings can cause "mechanical blockage" conditions of the drill battery (BHA);
- in the presence of wells with a high slope angle, in extended reach wells and in wells with a horizontal development, the drill cuttings have sufficient time to deposit on the lower part of the hole;
- at the drilling restart, after the insertion of a new rod, the bit is "compelled" to re-perforate the bed of deposited cuttings at the well bottom, before being able to reach the virgin formation once again.

As specified above, in patent application IT-MI2005A001108, the same applicant claimed a device, called E-CD, which allows the pumping and consequently the fluid circulation in the well to be kept constantly active, during all the operative steps, necessary for effecting the addition of a new "single element" to the battery of rods, which allows drilling to be effected to a greater depth.

With the same procedure, it is possible to effect the reverse process, allowing the bit to be extracted without interrupting the pumping of fluid into the well.

The key result which is obtained from this operative opportunity offered by the device is the elimination (or abatement) of all the critical aspects implied in the traditional process for adding or subtracting rods from the drill battery.

A description is provided hereunder of the E-CD device and the process for the insertion of a new drill string already described in patent application IT-MI2005A001108 cited above.

The device for the insertion of a new drill string essentially consists of a short body (C) in the form of a pipe having, at its ends, means suitable for being screwed onto drill rods, in which two valves are housed, of which one (A) is radial to said short body, which can be intercepted from the outside by means of an adapter and equipped with an appropriate safety top, preferably pressure-sealed, the other (B) axial to said body.

The result is a system of valves which allows direct contact to be made with the fluid pumped into the well through the drill battery, at any moment desired and in both directions of the descending fluid (radially and axially).

The short body of the device preferably has a length ranging from 50 to 100 cm.

The valve (A), which is radial to the drill battery, can be intercepted from the outside by means of a suitable adapter (for example a rapid connector), in turn coupled with a flexible pipe, whose function is to interconnect the device with the well pumping system ("Rig pump manifold"), of the drill plant itself.

As a consequence, the valve (B) which is axial to the drill battery and has characteristics of "bidirectional reactivity sensitivity" to the pressure to which it is subjected (therefore sensitive to the flow state of the drill fluid pumped into the well), in turn closes and opens directionally with respect to the fluid.

Both the radial valve (A) and the axial valve (B) are preferably butterfly valves, more preferably preloaded with springs, which are closed when in stand-by.

In short, the configuration of the two valves housed in a short body, as described so far, allows a flow of drill fluid to be easily kept uninterrupted towards the well, during all the operative steps necessary for effecting the addition of a new "single rod element" (or series of rods) to the drill battery, which allows drilling to be effected to a greater depth.

Apart from the conceptual and constructive simplicity, one of the intrinsic advantages of the device described above is that it can be immediately used by any drill plant, without requiring heavy modifications to the hydraulic circuit of the plant itself, or problems associated with the "vertical spatiality" for the insertion of the tool into the drill battery.

The device can be used in any type of plant existing in the world—with no exception—whether it be extremely obsolete or completely modern, whether it be equipped with the traditional "Rotary Table System" or more modern "Top Drive System", in both onshore and offshore well drilling.

Higher operating pressures can obviously be obtained by selecting higher-quality single components, to assemble the desired component.

There are numerous benefits deriving from the fact of not interrupting the circulation, and they can vary each time in relation to the type of well to which the procedure is applied.

In any case, the benefit which is common to all types of wells is the resulting constant pressure state on the walls of the hole and at the well bottom, which provide valuable intrinsic safety.

Let us examine in particular High Pressure and High Temperature Wells (HPHT).

In this type of well, the fracturing gradient of the formations penetrated, close to the mineralized rock (reservoir), is generally close to the value of the pore gradient. For this reason, a careful control of the ECD (equivalent circulating density) is compulsory to avoid circulation losses and structural weakening of the formation itself.

During interruptions in the circulation (necessary for effecting a conventional connection), the ECD is annulled, creating the ideal condition for the undesired entry of state fluid into the well (influx).

The influx can come directly from the reservoir (primary porosity) or from induced microfractures; in any case observation of the phenomenon (and the identification of the condition necessary for a new connection) implies a waste of operative and consequently unproductive time.

The "uninterrupted circulation" by means of the device described above, on the contrary, guarantees undisturbed dynamic conditions, allowing the safe and immediate insertion of a new rod, without any time losses.

Let us examine in particular the application for drilling defined as under Balance/Close to Balance Drilling (UBD).

For Underbalance drilling (UBD) and its derivatives, it is crucial to maintain a stable and controlled condition of the pressure regime, distributed on the walls of the hole as also on the well bottom.

The loss of this condition can jeopardize what has so far been effected upstream for UBD drilling. The addition of a rod to the drill battery is a particularly critical moment; the use of the device described above eliminates all critical aspects as soon as they arise, as it always guarantees undisturbed dynamic conditions, allowing the safe and immediate insertion of a new rod, without any time loss. The guarantee of maintaining a stable and constant pressure regime on the walls of the hole and well bottom, avoids the accumulation of gas cushions and "packs" of cuttings which would require non-productive time for eliminating them and re-establishing the stabilized conditions prior to the interruption of the circulation. An error in the running of this process leads to the risk of thwarting the whole UBD well project, activating an undesired accidental well killing.

An alternative to the use of the device can be to directly integrate the valve system forming the device itself in the construction phase of the drill rod; this alternative allows the length of the combination (rod+device) to be kept identical to that of a nude rod, should the necessity arise.

In any case, composed lengths of drill rods equipped with the device, will house the system at the head of any length. An alternative to the device can therefore be a drill rod essentially consisting of a pipe having suitable threadings at the ends to be screwed onto other drill rods, in which two valves are housed of which one (A) radial to said pipe, which can be intercepted from the outside by means of an adaptor and equipped with a suitable safety top, preferably pressure sealed, the other (B) axial to said pipe.

Both the radial valve (A) and the axial valve (B) housed in the rod are preferably butterfly valves, more preferably preloaded with springs, which are closed in stand-by.

The process for the insertion of a new drill string consists in using the devices described above or alternatively the drill rods described above in which there are radial and axial valves.

More specifically, this process preferably comprises the following steps:
intercepting from the outside and connecting by means of suitable means to the pumping system of the drill plant, the radial valve (A) of the short body or drill rod by means of a suitable connector;

voluntarily interrupting the flow of primary fluid, through the injection head, at the inlet in the drill battery with the consequent passage of the flow only from the radial valve (A) and with the consequent closing of the axial valve (B);

inserting a new drill string on the short body or drill rod, coupled with another short body in which said valves are housed or a new drill string containing a drill rod in which said valves are housed;

re-establishing the flow of primary fluid with the consequent opening of the axial valve (B) and consequent closing of the radial valve (A);

disconnecting the connector and protecting the radial valve (A) with a safety top;

lowering the drill battery.

Lastly, the final result of the operative steps described allows the insertion and connection process of an element in a drill battery (single rod or length) to be obtained, with a full flow-rate and without any interruption of the continuity.

From what is indicated above the term E-CD device in the present patent application comprises both the device and the drill rods, in which radial and axial valves are present, which form an alternative, claimed in patent application ITMI2005A001108.

BRIEF SUMMARY OF THE INVENTION

In order not to jeopardize the functionality of the probe valves of the well pumping system (Rig pump manifold) present on the drill plant during the use of the E-CD device, a new piece of equipment is now described for intercepting and diverting a liquid circulation flow which exerts the function of safely diverting the mud flow, during the changing of rods, towards the E-CD valves, without influencing the Rig Pump Manifold of the Rig Contractor which consequently maintains its functional characteristics intact.

The equipment, object of the present invention, for intercepting and diverting the liquid circulation flow, called "E-C Manifold", consists of three flow chambers and a series of valves, said chambers, equipped with connection means with arrival or supply lines, communicating with each other, of which only one (I) communicates with both of the other two (II)(III), the communication between said chambers each being obtained by means of at least two valves of which one is a flow-rate valve (Q) and at least one equalizer (E), each equalizer valve (E) being coupled, upstream or downstream thereof, with fixed or adjustable flow-blocking devices (D), the two non-communicating chambers having a valve (V) or a three-way valve in common, or one each, a one-way valve in counterposition, one being open when the other is closed and vice versa, said valve (V) being coupled with a discharge valve (S).

The flow-blocking devices (D) are preferably downstream of the equalizer valves.

The one-way valves in counterposition with respect to each other or the three-way valve (V) can be optionally coupled downstream with fixed or adjustable flow-blocking devices (D).

The installation of the equipment according to the invention does not require structural modifications to the drill plant. This equipment functions with compressed air on each drill plant (the compressed air activates an air motor which in turn entrains a hydraulic pump, thus generating a source of hydraulic oil fluid under pressure, which in turn activates the valves).

The recommended use of a control board facilitates the control of the various valves forming the equipment claimed.

At the end of the operation with the E-CD device, the equipment claimed is removed and the drill plant configuration returns to its original state.

In high-pressure operations, where it is essential to keep the well circulation pressure absolutely constant, an implement to the standard configuration has been conceived, which envisages the possibility of filling the "Top Drive side" with a low-pressure fluid, before opening the valve $E_2$ which equalizes the pressures between the chambers I and II.

This function is important when adding a new length of drill rod to the battery, as the length is screwed "empty" onto the E-CD valve, in the well at the probe level. The filling prior to the pressure equalization (effected by opening the valve $E_2$) eliminates the water hammer, avoids subtracting a useful flow-rate of fluid directed into the well, reduces the total time necessary for adding a new length of drill rods to the battery.

The hydraulic pistons which operate the valves receive hydraulic energy from an oil pump, in turn fed by a compressed air motor, which is activated for each use. The hydraulic energy can, in a future development, be supplied by a hydraulic accumulation (nitrogen pressure cylinder, with a separating membrane between nitrogen and hydraulic oil) which will allow numerous operations before having to be recharged. Its recharging will be effected by means of a pump/compressed air motor system, such as that currently used.

A further object of the present invention relates to the process for the insertion of a new drill string of a well using an E-CD device, or essentially consisting of a short body (C) having the form of a pipe or contained in drill rods essentially consisting of a pipe, said body or said pipe having, at its ends, threadings suitable for being screwed onto other drill rods and in which two valves are housed, of which one (A) is radial to said body or pipe, which can be intercepted from the outside by means of an adapter and equipped with an appropriate safety top, the other (B) axial to said body or pipe, which is characterized in that is also uses the equipment described above, which forms the main object of the invention.

The process for the insertion of a new drill string using the equipment described above comprises the following steps:

intercepting from the outside and connecting by means of suitable means to the pumping system of the drill plant, the radial valve (A) of the short body or drill rod by means of a suitable connector;

voluntarily interrupting the primary fluid flow, through the injection head, at the inlet in the drill battery with the consequent passage of the flow only from the radial valve (A) and with the consequent closing of the axial valve (B);

inserting a new drill string on the short body or drill rod, coupled with another short body in which said valves are housed or a new drill string containing a drill rod in which said valves are housed;

re-establishing the flow of primary fluid with the consequent opening of the axial valve (B) and consequent closing of the radial valve (A);

disconnecting the connector and protecting the radial valve (A) with a safety top;

lowering the drill battery.

The process for intercepting and diverting the fluid circulation flow coming from the plant pumps (Stand Pipe Manifold or Rig Pump Manifold) preferably uses the following steps in sequence:

"normal" circulation of said flow to the injection head (Top Drive) by entry into the chamber (I) of said equipment and exit from the chamber (II) connected with the line that leads to the injection head (Top Drive), passing through the open equalizer and flow-rate valves which put said chambers (I) and (II) in communication with each other, both the valves which allow communication between the chambers (I) and (III) and the discharge valve or valves (S) of the chambers (II) and (III) being closed;

start of the "double" circulation of said flow to the injection head (Top Drive) and E-CD device by entry into the chamber (I) and exit from both the chamber (II) connected to the line which leads to the injection head (Top Drive), passing through the open equalizer and flow-rate valves which put said chambers (I) and (II) in communication with each other, and also from the chamber (III) connected to the E-CD device passing through the open equalizer valve which puts the chambers (I) and (III) in communication with each other, both the flow-rate valve which allows communication between the chambers (I) and (III) and the discharge valve or valves (S) of the chambers (II) and (III) being closed;

"double" circulation transitory of said flow to the injection head (Top Drive) and to the E-CD device by entry into the chamber (I) and exit from both the chamber (II) connected to the line which leads to the injection head (Top Drive), passing through the open equalizer and flow-rate valves which put said chambers (I) and (II) in communication with each other, and also from the chamber (III) connected to the E-CD device passing through the open equalizer flow-rate valves which put the chambers (I) and (III) in communication with each other, the discharge valve or valves (S) of the chambers (II) and (III) being closed;

circulation of said flow only to the E-CD device by entry into the chamber (I) and exit from the chamber (III) connected to the E-CD device passing through the open equalizer and flow-rate valves which put said chambers (I) and (III) in communication with each other, both the valves which allow communication between the chambers (I) and (II) and the discharge valve or valves (S) of the chambers (II) and (III) being closed;

circulation of said flow only to the E-CD device as in the previous step and contemporaneous depressurization of the chamber (II) effected by opening the discharge valve (S) of the chamber (II);

start of the "double" circulation of said flow to the injection head (Top Drive) and E-CD device by entry into the chamber (I) and exit from both the chamber (II) connected to the line which leads to the injection head (Top Drive), passing through the open equalizer valve which puts said chambers (I) and (II) in communication with each other, and also from the chamber (III) connected to the E-CD device passing through the equalizer and flow-rate valves which put the chambers (I) and (III) in communication with each other, both the flow-rate valve which allows communication between the chambers (I) and (III) and the discharge valve or valves (S) of the chambers (II) and (III) being closed;

"double" circulation transitory of said flow to the injection head (Top Drive) and to the E-CD device by entry into the chamber (I) and exit from both the chamber (II) connected to the line which leads to the injection head (Top Drive), passing through the open equalizer and flow-rate valves which put said chambers (I) and (II) in communication with each other, and also from the chamber (III) connected to the E-CD device passing through the equalizer and flow-rate valves which put the chambers (I) and (III) in communication with each other, the discharge valve or valves (S) of the chambers (II) and (III) being closed;

re-establishment of the "normal" circulation of said flow to the injection head (Top Drive) and contemporaneous depressurization of the chamber (III) effected by opening the discharge valve (S) of the chamber (III), by entry into the chamber (I) of said equipment and exit from the chamber (II) connected to the line which leads to the injection head (Top Drive), passing through the open equalizer and flow-rate valves which put said chambers (I) and (II) in communication with each other, the valves which allow communication between the chambers (I) and (III) being closed.

DETAILED DESCRIPTION OF THE INVENTION

Figure 1:
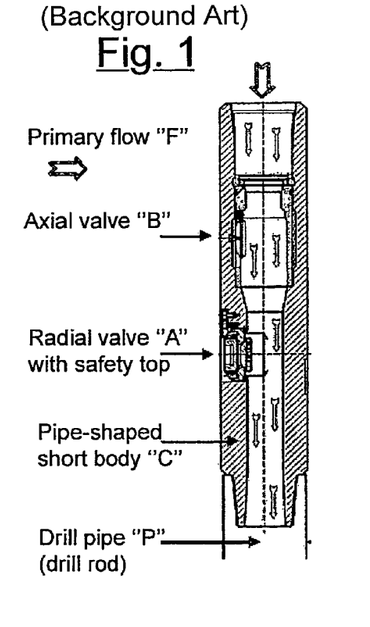
FIG. 1 shows a cross sectional view of a background art E-CD device in one aspect of a drilling phase.
Figure 2:
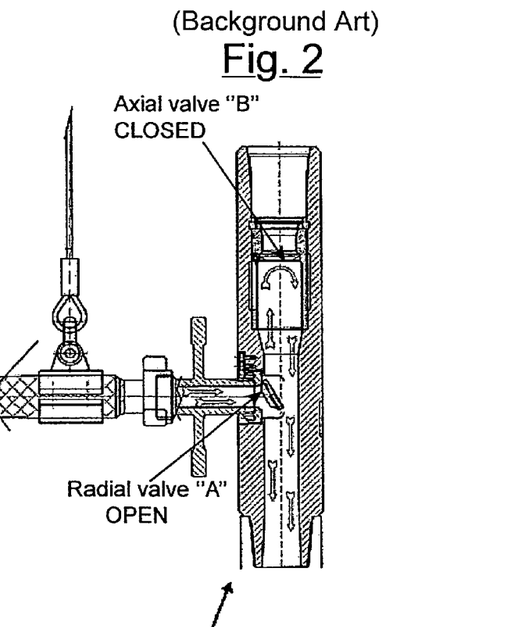
FIG. 2 shows a cross sectional view of the background art E-CD device in another aspect of the drilling phase.
Figure 3:
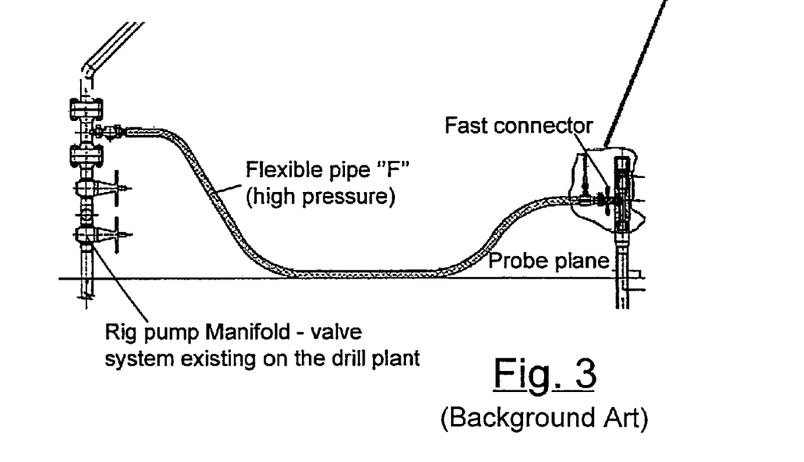
FIG. 3 shows a schematic view of a connection system of the background art E-CD device with a well pumping system.

A description is now provided of the E-CD device described in the above-mentioned patent application IT-MI2005A001108, with the help of FIGS. 1, 2 and 3.

FIG. 1 shows the E-CD device during the drilling phase in which only the primary flow (F) axially passes through the device.

FIG. 2 shows the E-CD device during the drilling phase in which the primary flow (F) is interrupted, whereas the secondary flow enters the device radially.

FIG. 3 shows the connection system of the E-CD device with the well pumping system.

The device in FIG. 1 has a short body (C) which essentially consists of a pipe in which two valves are housed of which one (A) is radial to said short body, closed, and the other (B), open, is axial to the short body.

Said device is screwed to a traditional drill rod (P). In FIGS. 2 and 3 the same device has the axial valve closed, whereas the radial valve is opened, intercepted from the outside by means of an adapter, which can be a fast connector, in turn coupled with a flexible pipe (F), whose function is to interconnect the device with the well pumping system (Rig pump manifold), of the drill plant itself.

In order to effect the connection, i.e. the addition of a single rod (or a whole length of rods) to the drill battery, without interrupting the pumping of the drill fluid into the well, it is necessary to interrupt this primary flow with a particular strategy, at the beginning of the process, and simultaneously substitute it with an equivalent flow, entering the battery of drill rods below the segregation point of the flow, generated by the device.

This necessity is helped by the combination of the two valves inside the device itself, suitably positioned axially and radially with respect to the drill battery.

Once the valve (A) radial to the drill battery has been intercepted from the outside and connected to the flexible pipe, and therefore to the whole well pumping system of the drill plant (Rig pump manifold), the drill fluid at the inlet of the well can intercept two independent and distinct flow runs, one axial and the other radial to the drill battery.

By subsequently voluntarily interrupting the primary fluid flow at the inlet of the drill battery, obtained by closing the corresponding valve on the Rig pump manifold, the valve "B" of the device consequently closes and the whole flow coming from the plant pumping system is compelled to pass from the radial valve "A" of the device, without any other direct intervention from the outside.

At this point of the process, the pressure segregated upstream of the axial valve "B" of the device can be released at atmospheric pressure (for example, through the discharge valve of the Rig pump manifold) obtaining the condition necessary for safely effecting the connection of a single rod (or a whole length of rods) in the drill battery.

Once the connection has been effected, the repetition in an inverse order of the sequence, will re-establish the flow towards the primary path, i.e. through the valve "B" of the device.

Figure 4:
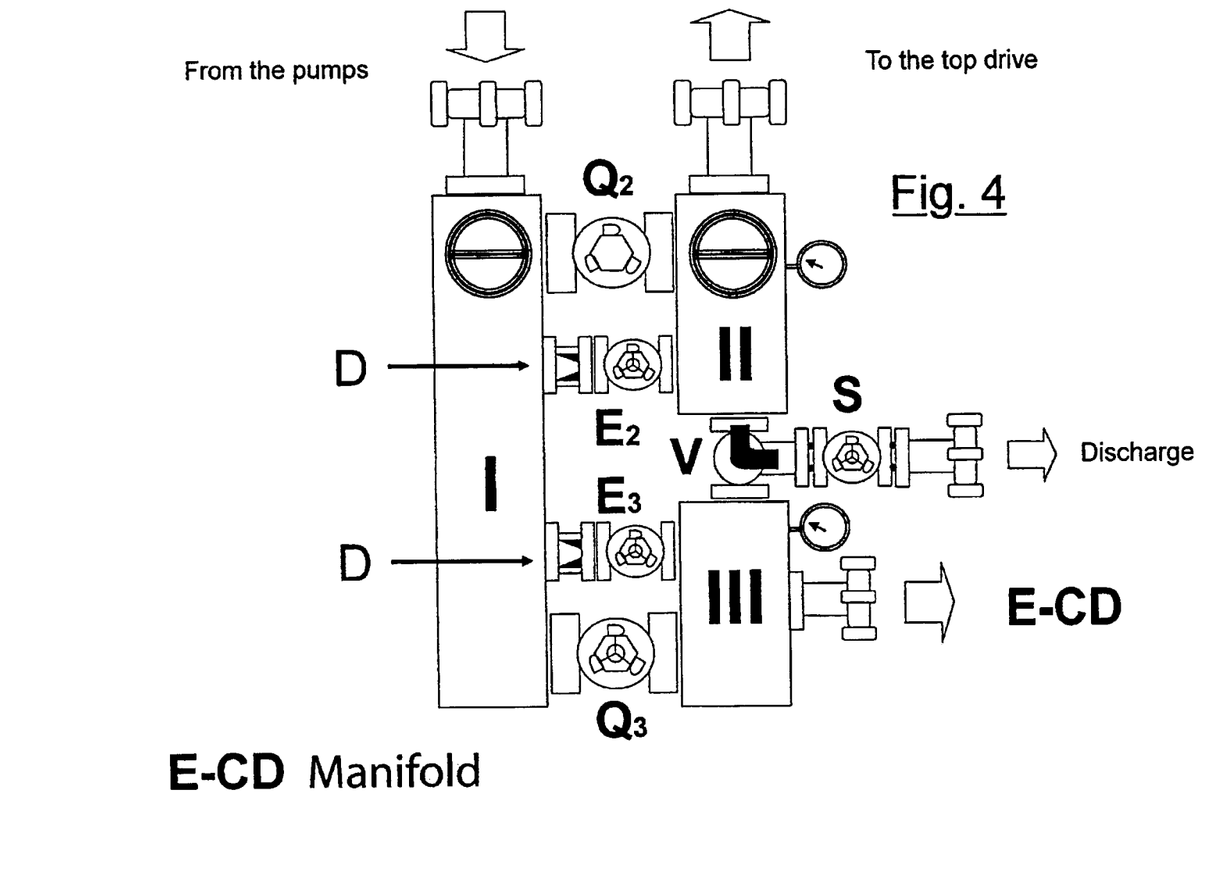
FIG. 4 shows a schematic view of an E-CD device according to the present invention.
Figure 5:
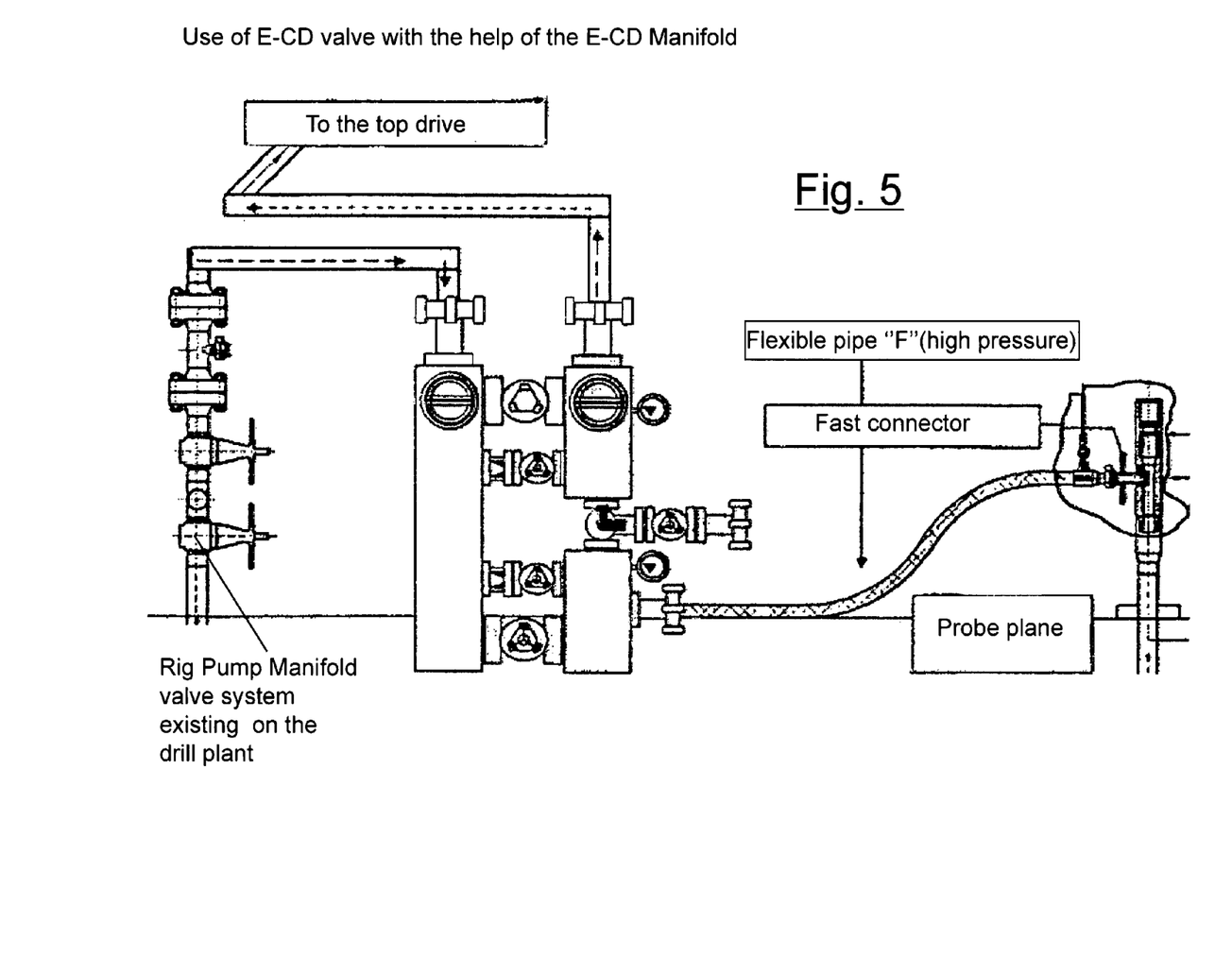
FIG. 5 shows a schematic view of a connection system of the E-CD device according to the present invention with a well pumping system.

An embodiment of the present invention is now described with the help of FIGS. 4, 5 and 6.

FIG. 4 shows the equipment called E-CD Manifold.

For intercepting and diverting a liquid circulation flow, the equipment consists of three flow chambers (I) (II) and (III) and a series of valves assembled on skids and hydraulically activated.

Said chambers are equipped with connection means with arrival lines (from the Pumps for the chamber (I) or supply lines (to the Top Drive for the chamber (II) and E-CD device for the chamber (III).

Said chambers communicate with each other, but only one (I) communicates with both of the others (II)(III): the communication between the chambers (I) and (II) and (I) and (III) are each effected by means of two valves of which one is a flow-rate valve (Q) and one an equalizer valve (E) ($Q_2$ and $E_2$ with the chamber (II) and $Q_3$ and $E_3$ with the chamber (III)).

The equalizer valves $E_2$ and $E_3$ are coupled with fixed or adjustable flow-blocking devices (D).

The two non-communicating chambers (II) and (III) have a three-way valve (V) in common with each other, coupled with a discharge valve (S).

FIG. 5 shows the connection system of the E-CD device with the well pumping system with the help of the E-CD Manifold.

Figure 6A:
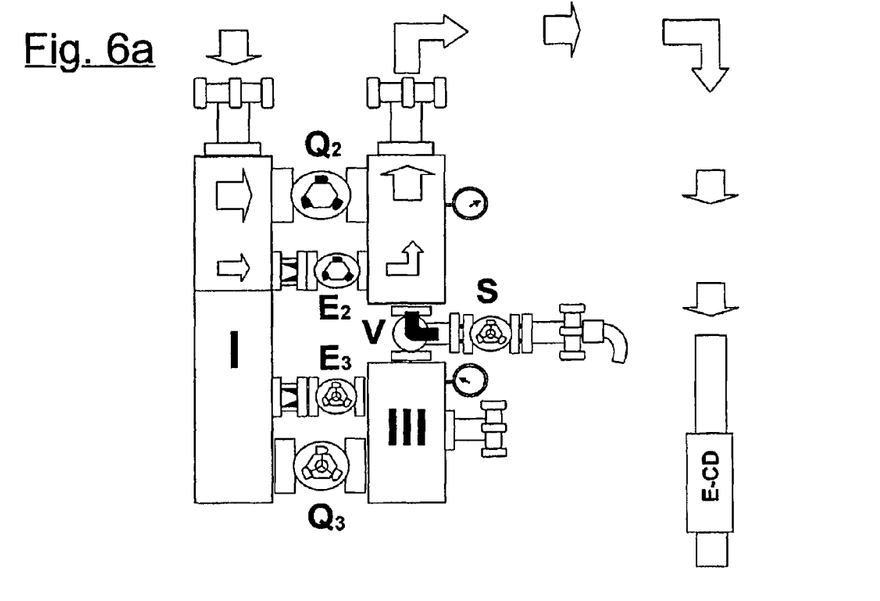
FIGS. 6a-h show schematic views the E-CD device according to the present invention during eight operations a) to h) of the device.

FIG. 6 graphically shows the involvement of the chambers (I), (II) and (III) and valves in managing the drill fluid flow (mud), under pressure, in the run from the Drill Plant Pumps to the Top Drive, alternatively in the run from the Drill Plant pumps to the E-CD valve, and in the transitories between the two runs.

a) "Normal" circulation to the Top Drive: the fluid enters the chamber (I) and leaves the chamber (II) passing through the valves $Q_2$ and $E_2$.

The valves $Q_3$, $E_3$ and S are closed.

Figure 6B:
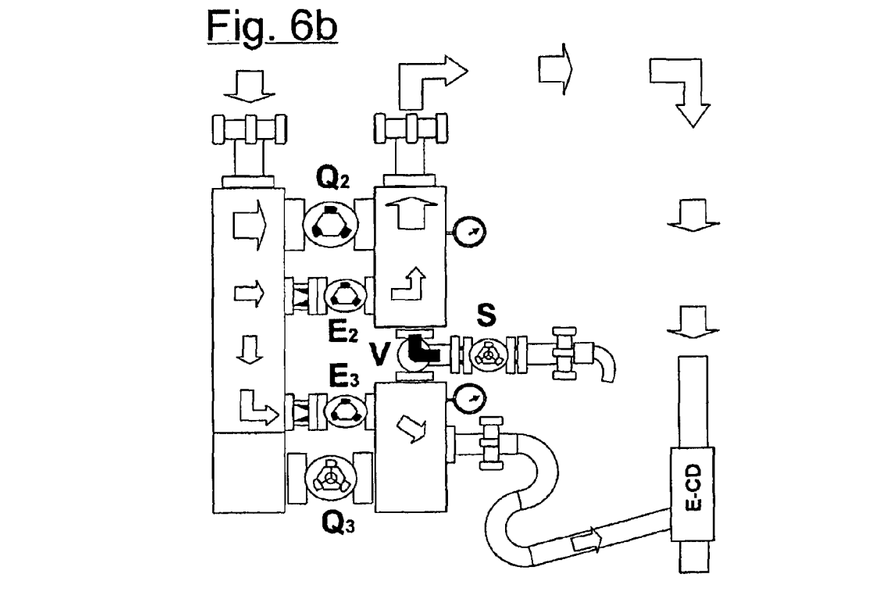
Figure 6C:
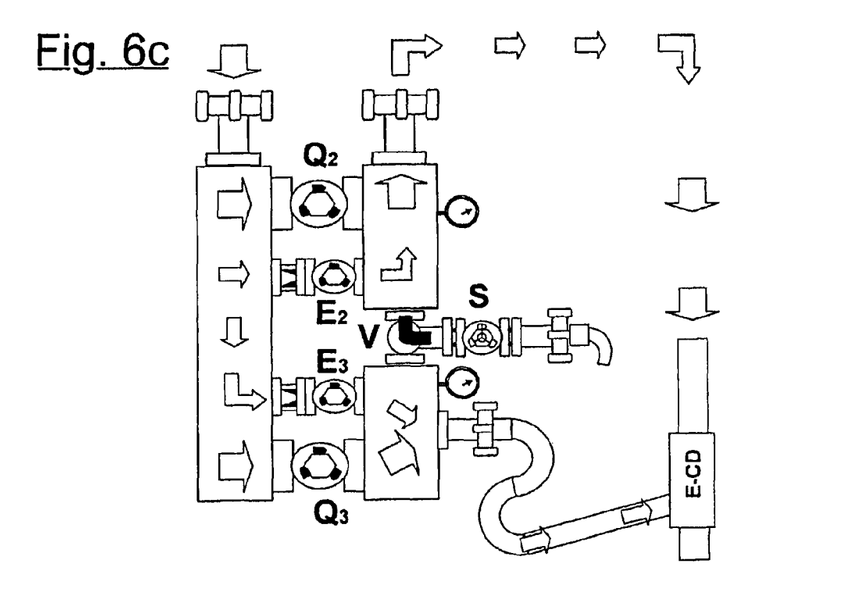
Figure 6D:
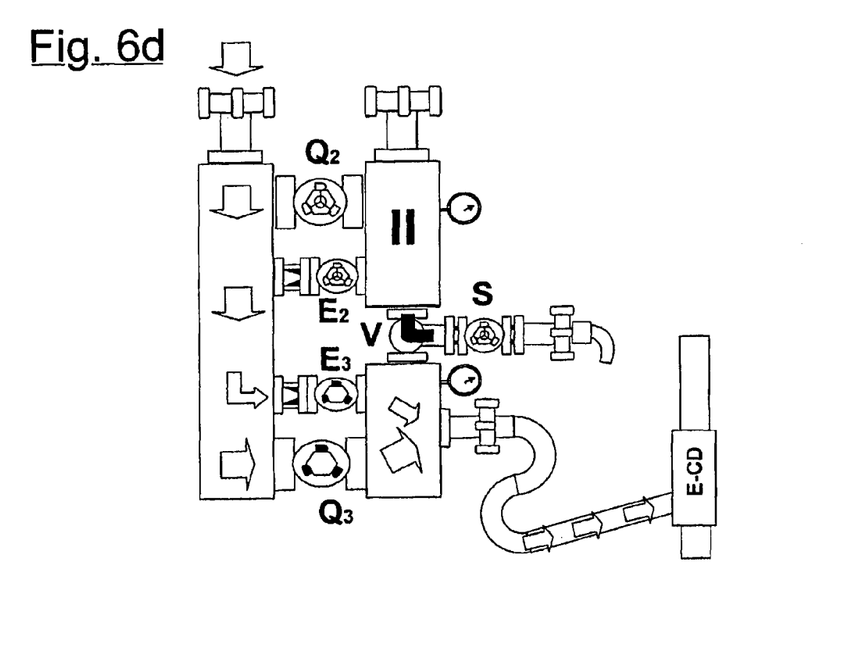
Figure 6E:
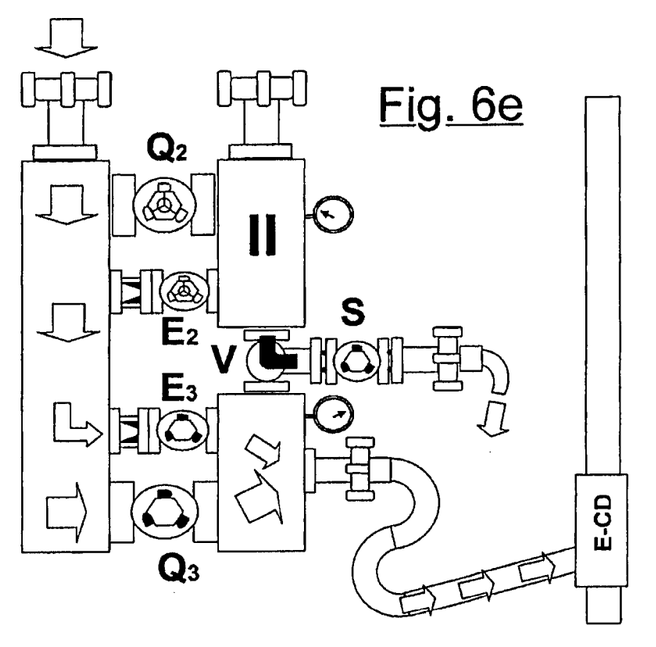
Figure 6F:
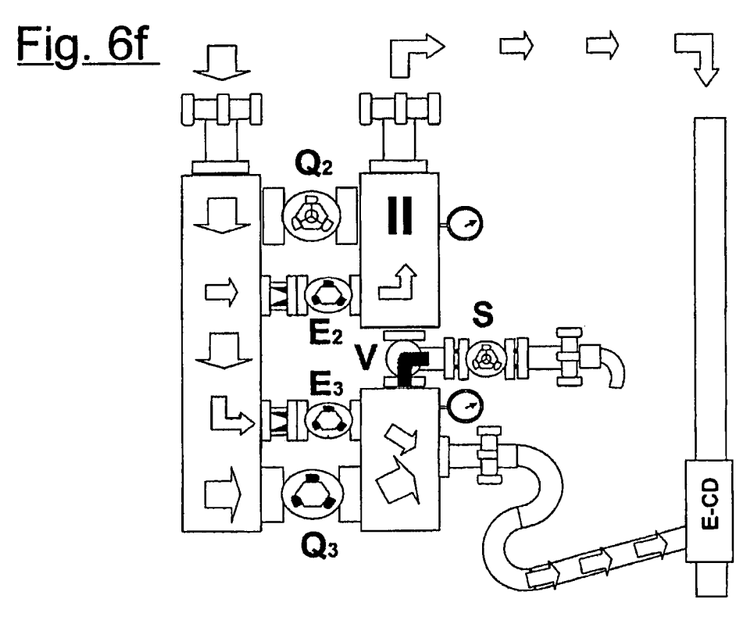
Figure 6G:
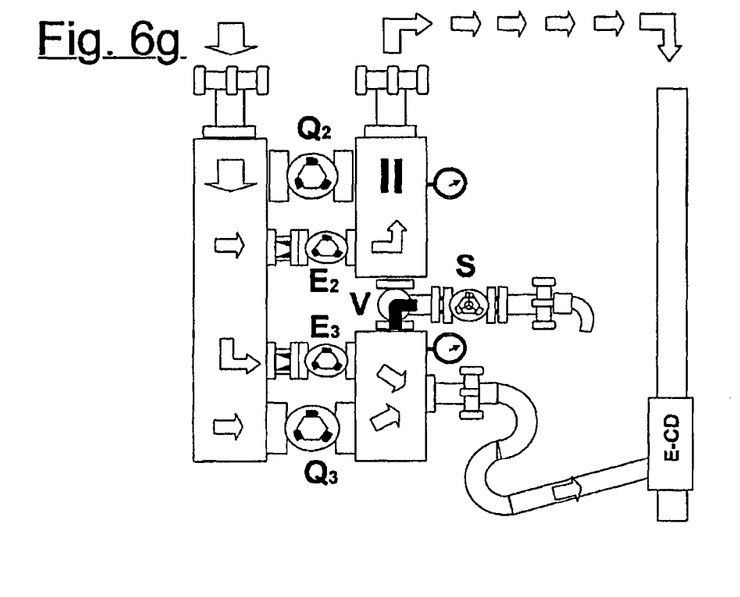

The chamber (III) is not pressurized.

b) Start of the "double" circulation to the Top Drive and E-CD valve: the valve $E_3$ has been opened, the fluid prevalently enters the chamber (I) and leaves the chamber (II); the pressurization is initiated of the chamber (III), which leads to the E-CD valve, which in the meantime has been connected to the chamber (III) with the flexible pipe.

c) "Double" circulation transitory to the Top Drive and E-CD valve: the fluid enters the chamber (I) and simultaneously leaves both chambers (II) and (III), without distinction. The valves $Q_2$, $E_2$ $Q_3$ and $E_3$ are all open, whereas the valve (S) is closed.

d) Circulation to the E-CD valve alone: the fluid enters the chamber (I) and completely leaves the chamber (III). The chamber (II) is intercepted by the valves $Q_2$ and $E_2$ which are closed; Segregated pressure remains in its interior. The valve (S) is closed.

e) Circulation to the E-CD valve alone and depressurization of the chamber (II) effected by opening the valve (S). (The three-way valve (V) is in a position suitable for intercepting the chamber (II) and isolating (III)). When the operation has been completed, it is possible to add a new length of rods which is screwed above the E-CD valve.

f) Start of "double" circulation to the E-CD valve and Top Drive; the valve $E_2$ has been opened, the fluid enters the chamber (I) and prevalently leaves the chamber (III); the pressurization of the chamber (II), which leads to the Top Drove (which in the meantime has been screwed to the head of the new length of rods, previously screwed above the E-CD valve), is started through the valve $E_2$: the valve (S) is closed. The chambers (I) (II) (III) are pressurized.

g) "Double" circulation transitory to the E-CD valve and Top Drive: the fluid enters the chamber (I) and simultaneously leaves both chambers (II) and (III), without distinction. The valves $Q_2$, $E_2$, $Q_3$ and $E_3$ are all open, whereas the valve (S) is closed.

Figure 6H:
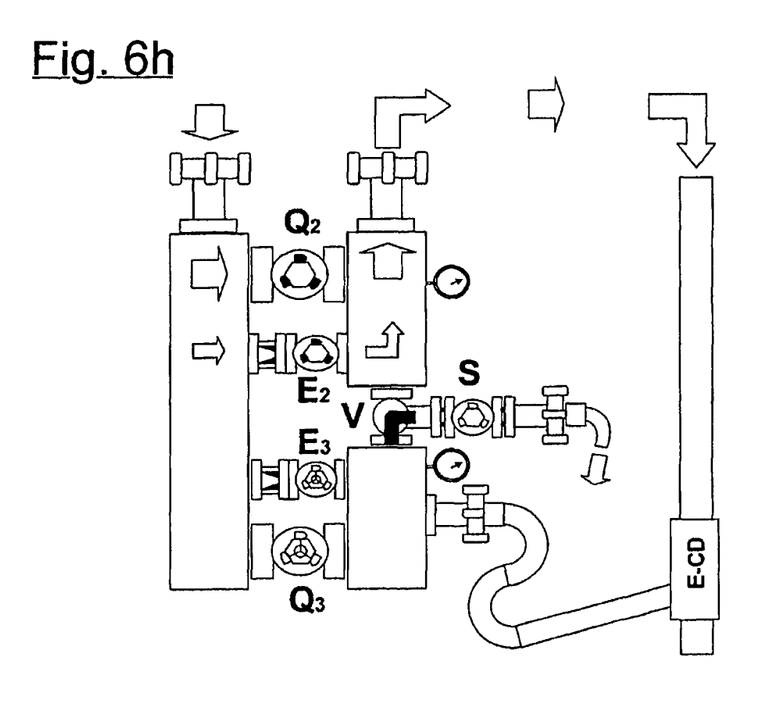

The three-way valve (V) has been maneuvered into a position which is suitable for intercepting the chamber (III) and isolating the chamber (II) (This can be effected also prior to step (f).

h) Re-establishment of the "normal" circulation to the Top Drive: the fluid enters the chamber (I) and completely leaves the chamber (II). The chamber (III) is intercepted by the valves $Q_3$ and $E_3$ which are closed. Segregated pressure remains in its interior. The valve (V) intercepts the chamber (III) and isolates the chamber (II). The valve (S) is opened to discharge the pressure segregated in the chamber (III).

Return to step (a) and end of the operating sequence: the drilling operation can now be re-established and will continue until the length of rods, which has just been added, has been entirely drilled.

Figure 7A:
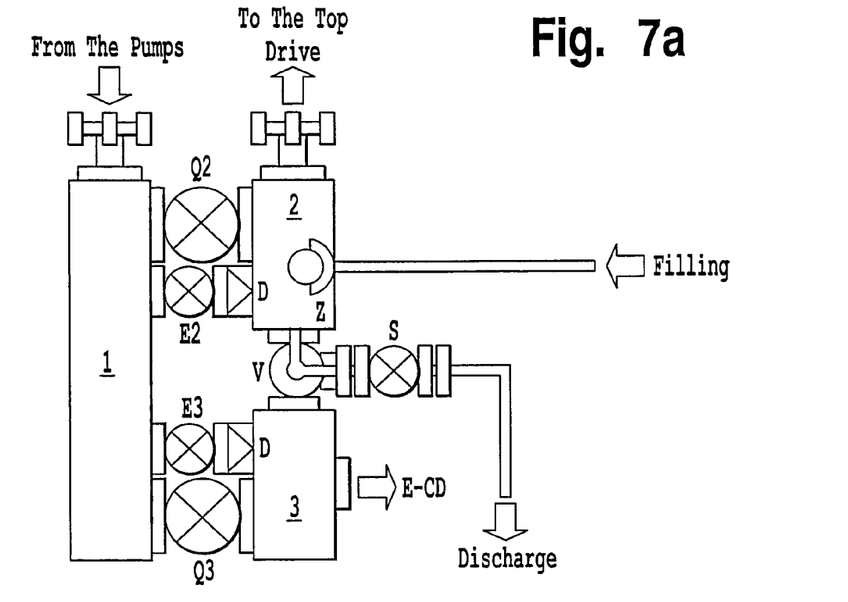
FIGS. 7a-b show schematic views of two E-CD devices according to further aspects of the present invention.
Figure 7B:
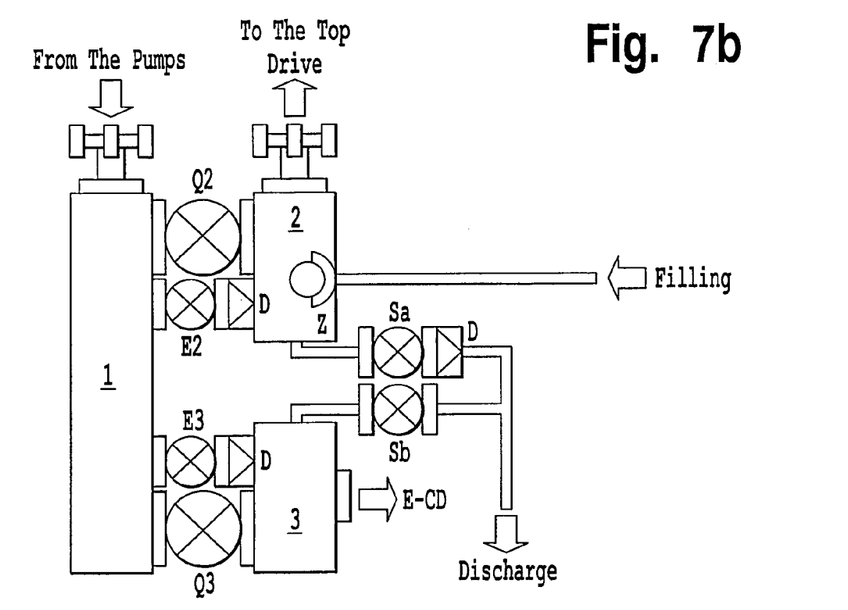

FIGS. 7a and 7b show illustrative examples in which chamber (2) of chambers (1), (2) and (3) includes a counter valve (Z). The counter valve (Z) is illustrated as a floating ball valve, although it can be substituted with a poppet valve, a flapper valve, or with any other counter valve (back pressure valve). In FIG. 7a, a three-way valve (V) is coupled to a discharge valve (S), and in FIG. 7b, two one-way valves (Sa) and (Sb) are in counterposition with respect to each other so that one is open when the other is closed.

A new E-CD valve is positioned at the head of the length, as for all the lengths that are subsequently added, and the sequence described is repeated.

The invention claimed is:

1. Equipment for intercepting and diverting a fluid circulation flow, comprising:
   three flow chambers and a series of valves,
   said chambers, equipped with a connection device with arrival or supply lines, communicating with each other, of which only a first flow chamber communicates with both of a second flow chamber and a third flow chamber, the communication between said first flow chamber and said second flow chamber and the communication between said first flow chamber and said third flow chamber each being obtained by at least two valves, of which one is a flow-rate valve and at least one is an equalizer valve, an upstream or downstream of each equalizer valve being coupled with a fixed or adjustable flow-blocking device, the second and third flow chambers being two chambers that do not communicate with each other and that include a three-way valve in common with each other, or that include two one-way valves in counterposition with respect to each other, one one-way valve being open when the other is closed and vice versa, said three-way valve or said two one-way valves being coupled with a discharge valve.

2. The equipment according to claim 1, wherein each fixed or adjustable flow-blocking device is downstream of one of the equalizer valves.

3. The equipment according to claim 1, wherein the one-way valves in counterposition with respect to each other or the three-way valve are coupled downstream thereof with one or more additional fixed or adjustable flow-blocking devices.

4. The equipment according to claim 1, wherein the second flow chamber includes a counter valve.

5. A process for the insertion of a new drill string of a well using an (Equivalent Circulating Density) E-CD device that includes a short body in the form of a pipe or that is contained in drill rods including a pipe, said body or said pipe having threadings at ends suitable for being screwed onto other drill rods and housing two valves, of which one valve is radial to said body or pipe and is interceptable from the outside by an adapter and equipped with a suitable safety top, the other valve being axial to said body or pipe, which comprises:
   intercepting and diverting the fluid circulation flow using the equipment according to claim 1.

6. The process for the insertion of a new drill string according to claim 5, wherein the intercepting and diverting the fluid circulation flow includes:
   intercepting from the outside and connecting the radial valve of the short body or drill rod to a pumping system of a drill plant, by a suitable connector;
   voluntarily interrupting a flow of primary fluid, through an injection head, at an inlet in a drill battery with a consequent passage of the flow only from the radial valve and with a consequent closing of the axial valve;
   inserting a new drill string onto the short body or drill rod, coupled with another short body in which valves are housed or a new drill string containing a drill rod in which valves are housed;
   re-establishing the flow of primary fluid with a consequent opening of the axial valve and a consequent closing of the radial valve;
   disconnecting the suitable connector and protecting the radial valve with a safety top;
   lowering the drill battery; and
   intercepting and diverting the fluid circulation flow from the pumping system of the drill plant.

7. The process according to claim 5 wherein, in order to intercept and divert a fluid circulation flow coming from a drill plant pumping system, which includes a Stand Pipe Manifold or a Rig Pump Manifold, the following steps are effected in sequence:
   conducting "normal" circulation of said flow to an injection head (Top Drive) by entry into the first flow chamber and exit from the second flow chamber connected with a line that leads to the injection head (Top Drive), passing through open equalizer and flow-rate valves which put said first and second flow chambers in communication with each other, both the equalizer and flow-rate valves which allow communication between the first and third flow chambers and the discharge valve or valves of the second and third flow chambers being closed;

starting "double" circulation of said flow to the injection head (Top Drive) and the E-CD device by entry into the first flow chamber and exit from both the second flow chamber connected to the line which leads to the injection head (Top Drive), passing through the open equalizer and flow-rate valves which put said first and second flow chambers in communication with each other, and also from the third flow chamber connected to the E-CD device passing through an open equalizer valve which puts the first and third flow chambers in communication with each other, both the flow-rate valve which allows communication between the first and third flow chambers and the discharge valve or valves of the second and third flow chambers being closed;

conducting "double" circulation transitory of said flow to the injection head (Top Drive) and to the E-CD device by entry into the first flow chamber and exit from both the second flow chamber connected to the line which leads to the injection head (Top Drive), passing through the open equalizer and flow-rate valves which put said first and second flow chambers in communication with each other, and also from the third flow chamber connected to the E-CD device passing through the open equalizer valve and an open flow-rate valve which put the first and third flow chambers in communication with each other, the discharge valve or valves of the second and third flow chambers being closed;

conducting circulation of said flow only to the E-CD device by entry into the first flow chamber and exit from the third flow chamber connected to the E-CD device passing through the open equalizer and flow-rate valves which put said first and third flow chambers in communication with each other, both the valves which allow communication between the first and second flow chambers and the discharge valve or valves of the second and third flow chambers being closed;

conducting circulation of said flow only to the E-CD device as in the previous conducting circulation step and contemporaneous depressurization of the second flow chamber effected by opening the discharge valve of the second flow chamber;

starting "double" circulation of said flow to the injection head (Top Drive) and the E-CD device by entry into the first flow chamber and exit from both the second flow chamber connected to the line which leads to the injection head (Top Drive), passing through the open equalizer valve which puts said first and second flow chambers in communication with each other, and also from the third flow chamber connected to the E-CD device passing through the equalizer and flow-rate valves which put the first and third flow chambers in communication with each other, both the flow-rate valve which allows communication between the first and third flow chambers and the discharge valve or valves of the second and third flow chambers being closed;

conducting "double" circulation transitory of said flow to the injection head (Top Drive) and to the E-CD device by entry into the first flow chamber and exit from both the second flow chamber connected to the line which leads to the injection head (Top Drive), passing through the open equalizer and flow-rate valves which put said first and second flow chambers in communication with each other, and also from the third flow chamber connected to the E-CD device passing through the equalizer and flow-rate valves which put the first and third flow chambers in communication with each other, the discharge valve or valves of the second and third flow chambers being closed;

conducting re-establishment of the "normal" circulation of said flow to the injection head (Top Drive) and contemporaneous depressurization of the third flow chamber effected by opening the discharge valve of the third flow chamber, by entry into the first flow chamber of said equipment and exit from the second flow chamber connected to the line which leads to the injection head (Top Drive), passing through the open equalizer and flow-rate valves which put said first and second flow chambers in communication with each other, the valves which allow communication between the first and third flow chambers being closed.

* * * * *